US012156647B2

(12) United States Patent
Rogers et al.

(10) Patent No.: US 12,156,647 B2
(45) Date of Patent: Dec. 3, 2024

(54) JOINT REPAIR AUGMENTATION

(71) Applicants: Smith & Nephew, Inc., Memphis, TN (US); Smith & Nephew Orthopaedics AG, Zug (CH); Smith & Nephew Asia Pacific Pte Limited, Singapore (SG)

(72) Inventors: Jon Paul Rogers, North Smithfield, RI (US); Michael Thyden, Billerica, MA (US); Stephen Anthony Santangelo, Sturbridge, MA (US); Ali Hosseini, Quincy, MA (US); Dennis Colleran, North Attleboro, MA (US)

(73) Assignees: Smith & Nephew, Inc., Memphis, TN (US); Smith & Nephew Orthopaedics AG, Zug (CH); Smith & Nephew Asia Pacific Pte Limited, Singapore (SG)

( * ) Notice: Subject to any disclaimer, the term of this patent is extended or adjusted under 35 U.S.C. 154(b) by 280 days.

(21) Appl. No.: 17/470,509

(22) Filed: Sep. 9, 2021

(65) Prior Publication Data

US 2022/0079576 A1    Mar. 17, 2022

Related U.S. Application Data

(60) Provisional application No. 63/192,383, filed on May 24, 2021, provisional application No. 63/078,541, filed on Sep. 15, 2020.

(51) Int. Cl.
*A61B 17/04* (2006.01)
*A61F 2/08* (2006.01)
(Continued)

(52) U.S. Cl.
CPC ........ *A61B 17/0401* (2013.01); *A61F 2/0811* (2013.01); *A61B 2017/00367* (2013.01); *A61B 2017/0409* (2013.01); *A61B 2017/0414* (2013.01); *A61B 2017/0446* (2013.01); *A61B 2017/0464* (2013.01); *A61B 17/0466* (2013.01); *A61F 2002/0823* (2013.01);
(Continued)

(58) Field of Classification Search
CPC ........ A61B 17/0466; A61B 2017/0409; A61B 2017/0414; A61B 2017/0446; A61B 2017/0464
See application file for complete search history.

(56) References Cited

U.S. PATENT DOCUMENTS 4,834,752 A   5/1989   Van Kampen
5,425,766 A   6/1995   Bowald
(Continued)

*Primary Examiner* — Alexander J Orkin
(74) *Attorney, Agent, or Firm* — Norman F. Hainer, Jr.

(57) ABSTRACT

Disclosed herein is a kit for augmenting a primary repair construct in an articulating joint. The kit includes a flexible member, a first implant that fixes a first end of the flexible member in a first bone adjacent to the primary repair construct and a second implant that may selectively couple to the flexible member, and thereby fix a second end of the flexible member in a second bone adjacent to the primary repair construct. The kit also includes a tension adjusting construct that may operatively couple to the flexible member and controllable adjust a tension on the flexible member disposed between the first and second implant, the tension adjustable so as to define an angle of joint articulation at which the flexible member changes from being passive to augment the primary repair construct.

21 Claims, 10 Drawing Sheets

(51) Int. Cl.
  *A61B 17/00* (2006.01)
  *A61F 2/30* (2006.01)
  *A61F 2/42* (2006.01)

(52) U.S. Cl.
  CPC ............... *A61F 2002/0852* (2013.01); *A61F 2002/0882* (2013.01); *A61F 2002/3069* (2013.01); *A61F 2/4202* (2013.01)

(56) References Cited

U.S. PATENT DOCUMENTS

| | | | | |
|---|---|---|---|---|
| 6,149,669 | A * | 11/2000 | Li | A61B 17/0401 606/68 |
| 6,780,198 | B1 * | 8/2004 | Gregoire | A61B 17/0401 606/232 |
| 9,999,449 | B2 | 6/2018 | Bonutti | |
| 11,457,958 | B2 | 10/2022 | Bonutti | |
| 2002/0019649 | A1 * | 2/2002 | Sikora | A61B 17/0401 606/232 |
| 2003/0023268 | A1 * | 1/2003 | Lizardi | A61B 17/0401 606/232 |
| 2003/0088272 | A1 * | 5/2003 | Smith | A61B 17/0401 606/232 |
| 2003/0204193 | A1 * | 10/2003 | Gabriel | A61B 17/0401 606/232 |
| 2004/0153075 | A1 * | 8/2004 | Roger | A61B 17/68 606/908 |
| 2004/0193217 | A1 * | 9/2004 | Lubbers | A61B 17/683 606/232 |
| 2006/0271060 | A1 * | 11/2006 | Gordon | A61B 17/0401 606/103 |
| 2007/0191849 | A1 * | 8/2007 | ElAttrache | A61B 17/0401 606/326 |
| 2007/0288023 | A1 * | 12/2007 | Pellegrino | A61B 17/0401 606/232 |
| 2008/0033460 | A1 * | 2/2008 | Ziniti | A61B 17/0401 606/148 |
| 2008/0147063 | A1 * | 6/2008 | Cauldwell | A61B 17/0487 606/60 |
| 2008/0188936 | A1 | 8/2008 | Ball et al. | |
| 2009/0069823 | A1 * | 3/2009 | Foerster | A61B 17/0401 606/228 |
| 2009/0326564 | A1 * | 12/2009 | White | A61B 17/06166 606/139 |
| 2012/0016428 | A1 * | 1/2012 | White | A61B 17/68 606/86 R |
| 2012/0109156 | A1 * | 5/2012 | Overes | A61B 17/0483 606/139 |
| 2012/0123416 | A1 * | 5/2012 | Gelfand | A61B 17/0401 606/139 |
| 2013/0096679 | A1 | 4/2013 | Laurencin et al. | |
| 2013/0131809 | A1 * | 5/2013 | Michielli | A61F 2/4455 623/17.16 |
| 2013/0190818 | A1 * | 7/2013 | Norton | A61B 17/0401 606/232 |
| 2013/0289730 | A1 | 10/2013 | Gabriel et al. | |
| 2013/0296936 | A1 * | 11/2013 | Burkhart | A61B 17/0401 606/232 |
| 2014/0142698 | A1 | 5/2014 | Landry et al. | |
| 2014/0277447 | A1 * | 9/2014 | Berelsman | A61B 17/0401 623/13.14 |
| 2014/0364862 | A1 * | 12/2014 | Bennett | A61B 17/0482 606/232 |
| 2015/0100121 | A1 | 4/2015 | Lu et al. | |
| 2016/0287746 | A1 | 10/2016 | Brulez et al. | |
| 2016/0374795 | A1 * | 12/2016 | Dougherty | A61B 17/0401 606/232 |
| 2017/0216016 | A1 * | 8/2017 | Sengun | A61B 17/0485 |
| 2018/0153601 | A1 * | 6/2018 | Riley | A61B 17/683 |
| 2018/0221010 | A1 * | 8/2018 | Lund | A61B 17/0401 |
| 2019/0029802 | A1 | 1/2019 | Van Kampen et al. | |
| 2024/0050083 | A1 | 2/2024 | Bonutti | |

\* cited by examiner

JOINT REPAIR AUGMENTATION

CROSS-REFERENCE TO RELATED APPLICATIONS

This application claims benefit to and incorporates by reference in its entirety, U.S. Provisional Patent No. 63/078,541, filed Sep. 15, 2020 and U.S. Provisional Patent No. 63/192,383, filed May 24, 2021; both titled "JOINT REPAIR AUGMENTATION".

FIELD

The present disclosure relates to methods and systems for augmenting a surgical repair. More specifically, it may relate to methods and systems for controlling a tension on a joint repair augmentation construct.

BACKGROUND

A primary repair, such as ligament repair or reconstruction surgery may be augmented with a secondary construct to improve surgical outcomes. Augmentation may involve placing the secondary construct in parallel with the primary repair. Augmentation may decrease failure of the primary repair and reduce the time needed for a patient to return to activity. Augmentation preferably guards against overly stressing the primary repair, without inhibiting healing of the primary repair. Augmentation may limit the stresses and strains on the primary repair or reconstruction, thereby reducing primary repair failure. For example, the secondary construct may limit loading on the primary repair when a patient stumbles and slightly twists their ankle. The reconstructed or repaired ligament however needs to experience some stress and cyclic loading to gain in mechanical fixation long term. Therefore, the secondary construct preferably allows the primary repair construct to undergo some stresses. For these reasons, there is an optimal target tension range that the secondary construct operates under, that helps the primary repair experience sufficient stress and thereby allow for ligamentalization, healing and strong mechanical fixation chronically, while mitigating ligament failure. Primary repairs may include ligament replacement or reconstruction, including ligaments such as the MCL, LCL, MPFL, lateral ankle ligament and/or acromioclavicular joint ligaments. More broadly, augmentation may provide secondary support for a repair of an articulating joint in the body, and may include a foot/ankle (both the deltoid ligaments, CFP ligament and forefoot ligament), a knee, a shoulder, or a wrist/hand.

Augmentation systems may include a flexible member, such as a suture, suture tape or a biological construct. Some attempted solutions have not sufficiently addressed the need to provide a secondary construct including a means for controlling a tension along the flexible member, and thereby more accurately maintain improved levels and limits of stresses on the primary repair, improving surgical outcomes. During the repair of smaller or thinner bones, fixation means may extend through these thinner bones and into joints adjacent thereto. Therefore, there is a need to provide fixation means that provide sufficient fixation while remaining reliably recessed away from external bone surfaces to avoid irritation of the adjacent articulating joints.

SUMMARY

Described herein are various improvements in methods and devices for augmenting a primary tissue repair. Such improvements include a plurality of suture anchors, that may be different from one another to provide a combination construct that allows for adjusting tension on a flexible member while the plurality of suture anchors are fixed within a tissue. Such improvements may also include a means of controlling the flexible member, and providing a controlled means of increasing or decreasing said tension. Improvements may include a combination construct that provides strong fixation in smaller bones near critical structures. Improvements may include a flexible member with improved mechanical properties for improved load sharing between the primary and augmenting construct.

An example kit is disclosed that may include a flexible member, a first implant or anchor configured to fix a first end of the flexible member in a first bone adjacent to the primary tissue repair location and a second implant configured to operatively couple to the flexible member, and fix a second end of the flexible member in a second bone adjacent to the primary repair construct. The kit also includes a means of controllably adjusting tension on the flexible member. The means may selectively couple to the flexible member extending from the first or second implant, and adjusts tension on the flexible member disposed between the first and second implant. Adjusting the tension is configured to adjust an angle of joint articulation at which the flexible member augments the primary repair construct.

In some example kit embodiments the flexible member is selected from a group including suture, suture tape or biological constructs. In some example kits, the biological construct may include a biodegradable biological construct. In some example kits, the biological construct may include a collagen based structure configured with mechanical properties that augment the primary repair construct; for example the collagen based structure may have a modulus of elasticity for improved load sharing between the primary and augmenting construct. In some example embodiments, the first implant may operably couple to the flexible member such that the flexible member may slide through the first implant when the first implant is fixed within the first bone. The first implant may include a pulley, and the flexible member may be looped around the pulley to operatively couple to the first implant. The first implant may be a rigid or an all-suture implant. The second implant may be a knotless anchor and the first implant may be defined as a non-locking anchor. The second implant may be inserted linearly, such that it does not require rotation during insertion and thereby maintains a target orientation of the flexible member extending between the two implants. This reduces twisting of the flexible member that may affect the tension thereon. The second implant may be operably coupled to the flexible member in two configurations; a first configuration that allows the flexible member to slide through the second implant when the second implant is fixed within the first bone and a second, locked configuration wherein the flexible member may no longer slide. In the first configuration, the flexible member may slide through the second implant to adjust the tension on the flexible member. In the second configuration, the knotless anchor may lock the augmenting construct at the target tension. The tension-adjusting construct may be coupleable to an insertion instrument of the second implant. The tension-adjusting construct may include an opening to receive and engage the flexible member and a handle for controllably adjusting tension along the flexible member. The handle may rotate to adjust the tension. The handle may increase or decrease tension on the flexible member.

An exemplary method of augmenting a primary repair construct associated with an articulating joint is also disclosed, the method including performing the primary tissue repair and augmenting the primary repair construct with a flexible member. Augmenting includes inserting a first anchor into a first bone adjacent a first anatomical attachment point of the primary repair construct, a flexible member slidingly coupled to the first anchor. The flexible member is also slidingly coupled to a second anchor. The second anchor is inserted into a second bone, adjacent a second anatomical attachment point of the primary repair construct. An end of the flexible member may be operatively coupled to a tension-adjusting construct and a tension on the flexible member adjusted. Once a target tension has been achieved, the flexible member is locked in place at the target tension via the second suture anchor. The target tension defines an angle of joint articulation at which the flexible member augments the primary repair construct.

In some example methods, the first anchor includes a pulley, and the flexible member is slidingly coupled around the pulley such that two flexible member ends exit the first anchor proximal end. The second anchor may be a knotless anchor. Adjusting the tension on the flexible member may be performed after fully inserting the first and second anchor and before locking the second anchor. The second anchor may be inserted with an insertion instrument that also includes the tension-adjusting construct. The tension-adjusting construct may be removably attached to the insertion instrument. The flexible member may be first operatively coupled to the tension-adjusting construct, or a portion thereof, before operatively coupling the tension-adjusting construct to the insertion instrument. Operatively coupling the flexible member to the tension adjusting construct may include coupling a first limb of the flexible member to a first adjustment actuator and a second limb of the flexible member to a second adjustment actuator, each adjustment actuator configured to tension independently. In some methods, adjusting the tension may also include articulating a patient joint associated with the primary tissue repair and then increasing or decreasing the tension on the flexible member. The tension may be adjusted such that the flexible member augments the primary construct at an angle of articulation that is at least 30 degrees.

Another example kit is disclosed for augmenting a primary repair construct of an articulating joint and may include a flexible member, a first implant configured to fix a first end of the flexible member in a first bone adjacent to the primary tissue repair location and a second implant configured to operatively couple to the flexible member, and fix a second end of the flexible member in a second bone adjacent to the primary repair construct. The flexible member is configured at a tension that defines a maximum load on the primary repair construct. The flexible member may be absorbed over time and thereby gradually increase the maximum load limit that the primary repair construct takes on over time. In some example embodiments, the flexible member comprises a collagen based construct.

Another example method of augmenting a primary repair construct of an ankle joint is disclosed, including inserting a soft anchor and flexible member into a talus bone and towards the subtalar joint at a location adjacent a first anatomical attachment point of the primary repair construct. The soft anchor is then deployed within the talus bone, such that the distal end of the soft anchor moves away from the subtalar joint. The deployed soft anchor is therefore entirely spaced away from the subtalar joint. The flexible member is then coupled to the second anchor, once the soft anchor is deployed. The second anchor is then inserted into a fibula of the ankle, adjacent a second anatomical attachment point of the primary repair construct. The flexible member is slideable through the second anchor, to adjust tension between the two anchors. Tension is adjusted between the first and second anchor and the flexible member locked with the second anchor, once the desired tension has been achieved. The flexible member extends between the two anchors and preferably does not coupled directly to a tissue or extend through any tissue (it preferably couples to the joint area via the anchors only). Stated in another way, the flexible member may not be a used to repair or reconnect a torn tissue for example. The flexible member may be knotlessly locked with the second anchor.

In some example embodiments, the method of augmenting also includes operatively coupling a limb of the flexible member to a tension-adjusting construct and adjusting a tension on the flexible member between the first anchor and second anchor with the tension-adjusting construct. Adjusting may occur after inserting the second anchor and before knotlessly locking the flexible member with the second anchor. In some example methods, adjusting the tension on the flexible member may include sliding the flexible member through the soft anchor. In some example methods, the tension-adjusting construct may be coupled to an insertion instrument for inserting the second anchor, after operatively coupling the flexible member limb thereto.

Another example method of augmenting a primary repair construct with a flexible member may include inserting a soft anchor into a first bone from a first side of the first bone and towards an opposing side (or opposing external surface) of the first bone, the inserting adjacent a first anatomical attachment point of the primary repair construct, the flexible member slidingly coupled to the soft anchor. The flexible member is then tensioned to deploy the soft anchor, wherein deploying engages a proximal end of the soft anchor against a cortical rim at the first side of the first bone and withdraws the soft anchor away from an internal joint bounded by the opposing side of the first bone. This recesses the soft anchor in its entirety from the internal joint. The flexible member is then coupled to a second anchor, so that the flexible member may slide through at least the second anchor. The flexible member may also be able to slide through the deployed first anchor. The second anchor is then inserted into a second bone adjacent a second anatomical attachment point of the primary repair construct and the flexible member is locked to prevent further sliding relative to the second anchor. The flexible member may be knotlessly locked with the second anchor.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1B:
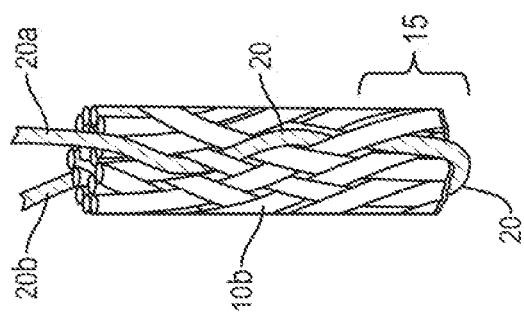
FIG. 1B illustrates another example anchor in accordance with this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Disclosed herein is a kit for augmenting a primary tissue repair of an articulating joint. The kit may include a plurality of anchors and at least one flexible member that couples to the plurality of anchors. It may also include a means of inserting the plurality of anchors with bone and a construct that couples to the flexible member and adjusts a tension on the portion of flexible member that extends between the anchors. Adjusting the tension on the flexible member may adjust the angle of joint articulation at which augmentation begins to initiate and supplement the primary repair. The at least one flexible member may include a suture, suture tape, ribbon, wire, or a synthetic or biologic construct. A first end anchor 10 of the plurality of anchors is configured to anchor within a first bone near a first end of primary tissue repair. Anchoring may include pounding the first anchor 10 into the bone, threadingly engaging the first anchor with the bone, or deploying the first end anchor 10 to selectively expand it into the first bone. The first end anchor 10 preferably also includes a means to couple with flexible member, and may be a non-locking anchor. A non-locking anchor is one that allows the flexible member to slide along the anchor while inserted within bone, and is not provided with a means or mechanism that prevents the flexible member from sliding. Anchors with transverse pulleys such as, but not limited to the Healicoil◊ anchor, offered by Smith and Nephew is an example non-locking anchor. All-suture anchors may also allow a flexible member to slide therethrough, while engaged with bone. Example all-suture anchors may include the Q-fix◊ or Suturefix◊, offered by the Smith and Nephew.

Figure 1A:
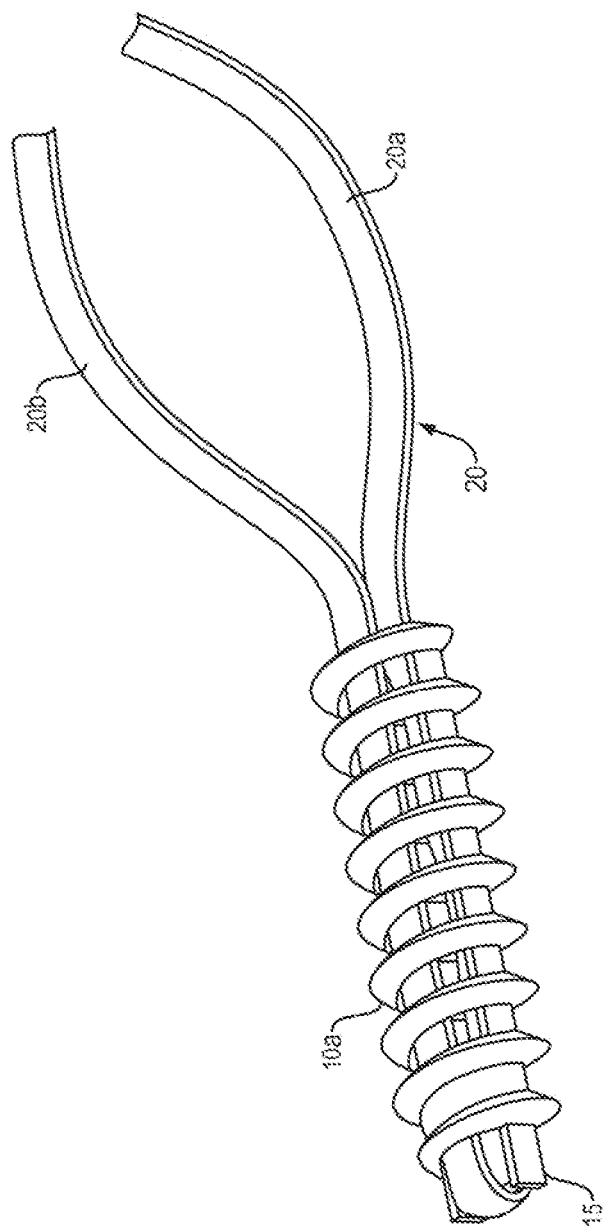
FIG. 1A illustrates an example anchor in accordance with this disclosure.

FIG. 1A shows an example rigid anchor 10a with a pulley 15 that may be a first end anchor 10 of the kit. Details of this example anchor 10a are disclosed in at least commonly owned U.S. Pat. No. 10,603,159, herein incorporated in its entirety by reference. Anchor 10a may be a rigid anchor, formed of a plastic such as PEEK for example. Flexible member 20 may extend along the anchor 10a and around pulley 15, such that two flexible member limbs 20a, 20b extend from proximal end of anchor 10a. Flexible member 20 may extend along a smooth internal lumen of anchor 10a, free from snagging or high friction points providing for easy sliding of the flexible member during manipulation. This reduces any friction or snagging on the flexible member 20, which could potentially frustrate the step of applying and assessing a tension of the augmentation construct. Pulley 15 may be disposed anywhere along the anchor 10a. As shown, it is at a distal end of anchor 10a. Pulley 15 may even out tension differentials between the two limbs 20a, 20b. Flexible member limbs 20a, 20b preferably extend from first end anchor 10 and along the primary repair, over an external tissue surface to the other side thereof, without twisting the flexible member 20.

FIG. 1B illustrates another example first end anchor 10 that may provide a pulley. This anchor may be a soft or all-suture anchor 10b. Example soft anchors 10b are disclosed in commonly owned U.S. Pat. No. 9,962,149; herein incorporated in its entirety by reference. In this example, flexible member 20 may intertwine through the anchor 10b and loop around or through an end of anchor 10b, defining a pulley portion 15. Distal most end of anchor 10b may define a sealed linear edge, around which the flexible member 20 may slide. Anchor 10b is softer and more deformable than example rigid anchor 10a, and may be formed of a soft flexible material such as, but are not restricted to, Ultra High Molecular Weight Polyethylene (UHMP). Polyester, Polyproylene, Silk or bioabsorbable materials typically used for suturing applications. Flexible member 20 may extend along the anchor 10b and around pulley portion 15 defined by an end of anchor 10b, such that two flexible member limbs 20a, 20b may extend from proximal end of anchor 10b. Having a pulley portion 15 may even out tension differentials between the two limbs 20a, 20b, during and after the augmentation construct is placed.

In alternative embodiments the first end anchor 10 may be a locking anchor (not shown) in that the flexible member 20 may be selectively locked, or prevented from sliding along the anchoring implant, either upon insertion into the bone, or via a locking means. Locking means may include a knot. Locking means may avoid a knot and utilize a plug member or moveable member to selectively trap and lock the flexible member 20 from sliding.

Figure 2C:
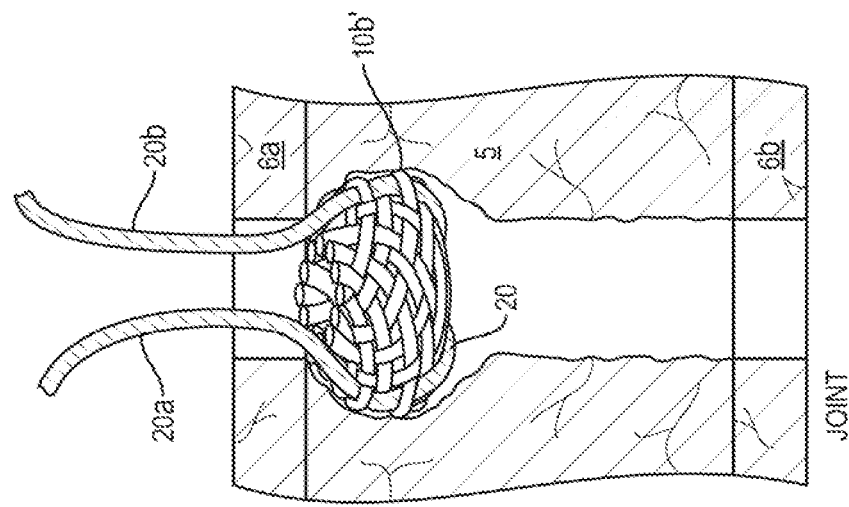
FIG. 2C illustrates a deployed soft anchor inserted into bone, in accordance with this disclosure.
Figure 2B:
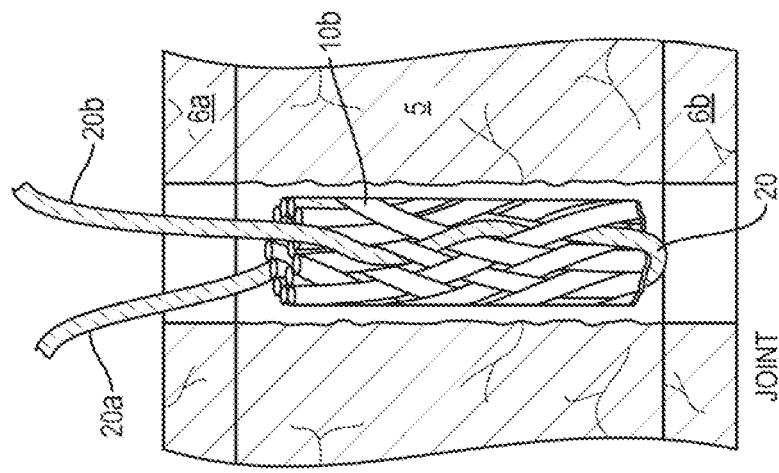
FIG. 2B illustrates an soft anchor inserted into bone not yet deployed, in accordance with this disclosure.
Figure 2A:
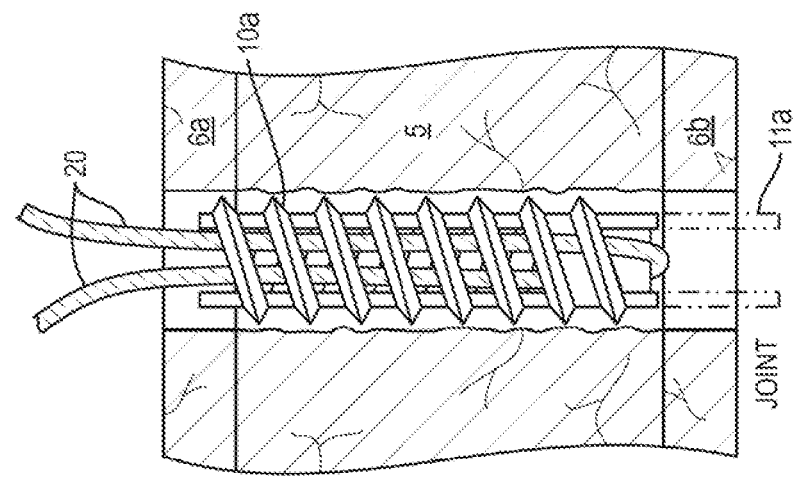
FIG. 2A illustrates a rigid anchor inserted into bone, in accordance with this disclosure.

In some joints with thinner or smaller bones, there may be an advantage to one of the plurality of anchors anchor being a soft anchor 10b. Turning to FIGS. 2A-2C, a comparison of a rigid and soft anchor (10a, 10b) is shown, with the anchors 10a, 10b inserted into a small bone such as the talus 5. FIG. 2A illustrates rigid anchor 10a inserted into the Talus 5, the thickness of the Talus 5 extending from a first cortical layer 6a to an opposing cortical layer 6b. Cortical layer 6b defines a boundary of the subtalar joint. Depending on the orientation of insertion of anchor 10a, together with the anatomy (thickness) of the talus 5 at the insertion point, the anchor 10a may extend through the opposing cortical layer 6b. In some cases, a rigid anchor has a length required for adequate fixation with the bone that is greater than the thickness of bone 5. Therefore, in some instances, a distal end of anchor 11a may extend through cortical layer 6b and protrude into subtalar joint (illustrated as a shadow/broken lines). In some examples, a surgeon may alter the angle of insertion of the anchor 10a to add effective thickness of the bone, and reduce protrusion into the joint. This may be technique dependent, and require use of extra tools, imaging and care to avoid protrusion into the joint. This may not always possible, depending on the anatomy.

For example, some rigid anchors may be 15-25 mm long and 3-5 mm in diameter, these dimensions considered necessary to gain good purchase on the bone. If the talus thickness for example is less than 15 mm for example, the anchor may protrude into the joint, which can cause pain, damage and/or irritation to the joint. Soft anchors in comparison are not only softer and therefore likely to cause less pain, damage or irritation, but some soft anchors are also significantly shorter in deployed length relative to rigid anchors for similar bone purchase strength. These may therefore reduce time and cost associated with extra steps and tools. FIG. 2B illustrates for comparison the same bone as illustrated in FIG. 2A, with the soft anchor 10b in an elongate configuration for easy insertion into the bone. In the elongate state, anchor 10b may be similar in length to rigid anchor 10a and may extend through some or all of bone thickness, and may protrude into joint area, depending on orientation of anchor insertion and talus anatomy. FIG. 2C illustrates the same soft anchor 10b within the same bone 5 as shown in FIGS. 2A and 2B in a deployed configuration 10b'. During deployment, the soft anchor 10b advantageously moves to engage a rim of the first cortical layer 6a and the soft anchor distal end moves away from joint. In comparison, in a deployed configuration, some soft anchors 10b' such as the one illustrated, extend as little as 4-6 mm below the cortical bone layer 6a. A soft anchor such as anchor 10b may therefore provide substantially similar or better fixation compared to rigid anchors, while requiring engagement within a significantly shorter length or thickness of the bone. This may, at a minimum, help avoid the extra steps, time and costs required to improve insertion of rigid anchors into smaller bones to avoid intrusion into the joint. In some bone anatomy, this shorter anchor may be the only way even with the extra steps and manipulation of the surgeon to avoid protrusion into the patient's joint area.

Figure 3A:
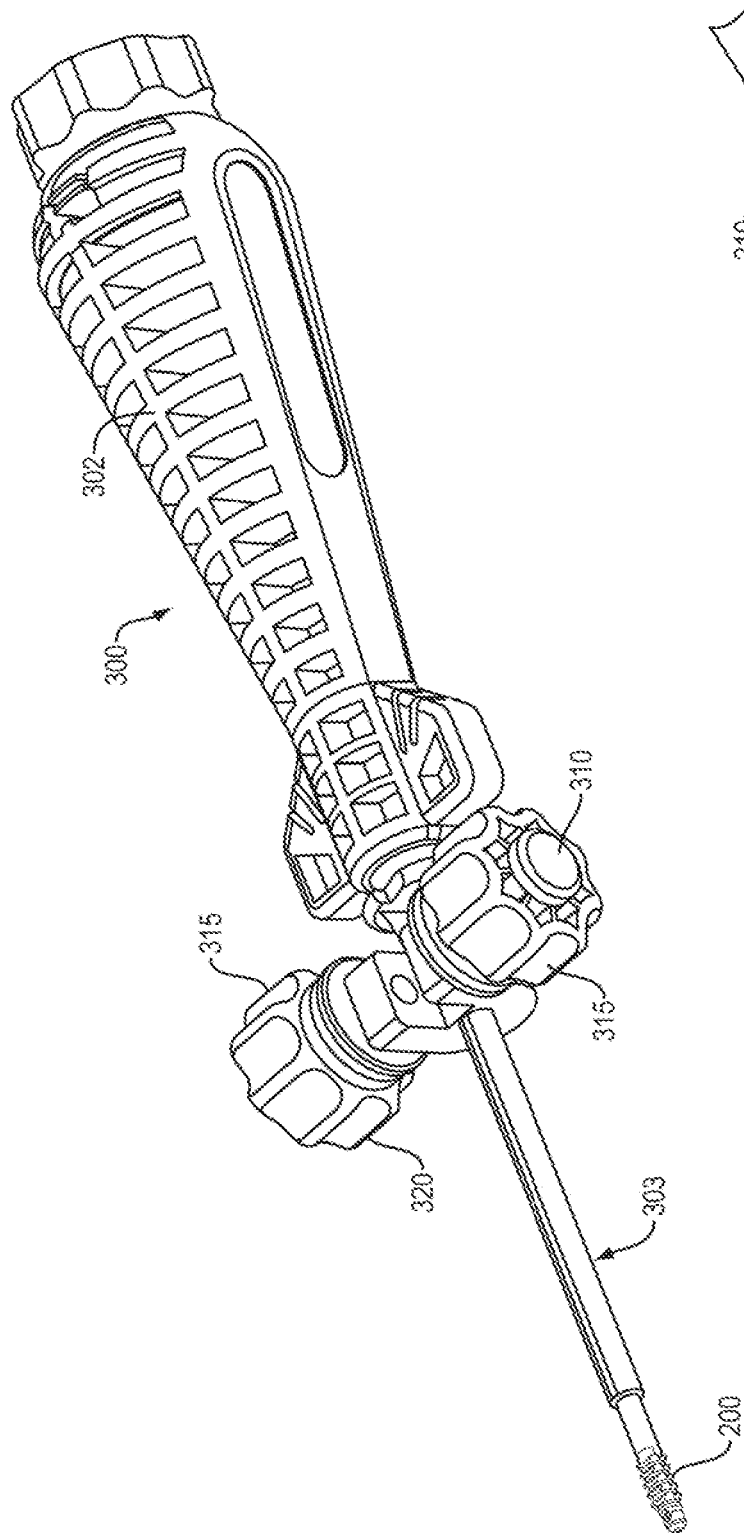
FIG. 3A illustrates an example second anchor of this disclosure.
Figure 3B:
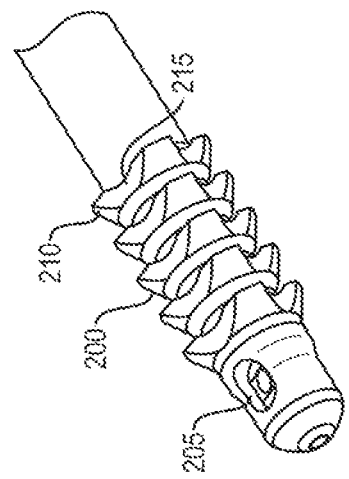
FIG. 3B illustrates an example anchor inserter with a tension adjusting member attached thereto, in accordance with this disclosure.

A second of the plurality of anchors may have a different configuration to the first end anchor 10. The second end anchor is configured to anchor with a second bone near a second (opposing) end of primary tissue repair. Anchoring may include pounding the anchor into the bone, threadingly engaging the bone, or deploying the anchor to selectively expand the anchor and thereby engage the bone. For reasons explained later, it is preferable that the second placed anchor not rotate during insertion. The second end anchor may include a means to thread the flexible member 20 therethrough. At least one of the two limbs (20a, 20b) that extends from the first end anchor 10 (such as example anchors 10a, or 10b) may be drawn or pushed through an opening of the second anchor, while the first end anchor is engaged with the first bone. Threading means may include a snare (not shown) operatively coupled to a through-hole of the second anchor, such that the flexible member 20 may be drawn through the through-hole. This second end anchor may have a first and a second configuration. In the first configuration, the flexible member 20 may slide through the second end anchor while the second end anchor is inserted into the bone. This may alter the tension of the flexible member between the first and second end anchors, and thereby alter the tension at which the augmentation construct supplements or relieves stresses on the primary repair. In the second locked configuration, the flexible member 20 may be prevented from sliding. Example anchors with through-holes and selective locking may include, but are not limited to the Bioraptor◇ or FootPrint◇ or Raptormite◇ Anchors, sold or provided by Smith and Nephew. FIGS. 3A and 3B illustrate an example second end anchor 200, a detailed description of which can be found in at least U.S. Pat. No. 9,936,939; commonly owned and incorporated by reference in its entirety.

Illustrated in FIG. 3B is an example second end anchor 200 with a through-hole 205 for receiving the flexible member 20 therethrough and barbs 210 for anchoring with prepared bone tunnel walls. In addition, anchor 200 includes an elongate external recess 215 or channeled area extending from the through-hole 205 to the proximal end of the anchor 200. Recess 215 is sized to provide a path for the flexible member 20 from the through hole 205 along the anchor 200, the recess 215 configured to allows the flexible member 20 to slide externally along the length of the anchor 200. The flexible member 20 may therefore slide along the anchor 200 while the anchor 200 is anchored within bone. This allows tension to be adjusted on the flexible member 20 between the two anchors (10 and 200). Upon the target tension being achieved, an internal axially moving plug (not shown) may be advanced along an internal lumen of the anchor 200 and across at least a portion of the through-hole 205, to knotlessly lock the tension on the flexible member 20. Both the first and second anchors are preferably less than 5 mm in maximum diameter, and more preferable less than 3 mm in maximum diameter.

In some example kits, the second anchor may also be a soft anchor, similar to anchor 10b for example. As discussed herein, some soft anchors have the advantage in that, upon deployment, they become very short. In a deployed configuration, soft anchors may extend as little as 4-6 mm below the cortical bone layer. Rigid anchors are typically over 10 mm long, and sometime up to 20 mm long, which in the case of the smaller bones of the extremities may not be available, or may significantly weaken the bone structure. Soft anchors that include knotless locking means are also disclosed in at least commonly assigned International Patent Application WO2020252372; filed Jun. 20, 2020, and titled "SOFT ANCHORING TISSUE REPAIR ASSEMBLY AND SYSTEM".

FIG. 3A illustrates an anchor inserter 300 for inserting anchor 200. Inserter 300 may include a tension adjusting construct 310. Anchor inserter 300 may directly couple to second anchor 200 and insert and couple second anchor 200 with the second bone. Anchor inserter 300 may also selectively actuate a knotlessly locking plug, as described herein and also in at least U.S. Pat. No. 9,936,939; commonly owned and incorporated by reference in its entirety.

Tension adjusting construct 310 may be removable from the inserter 300 or be provided integrated thereto. Tension adjusting construct 310 may be selectively snapped onto and off the anchor inserter 300. In some embodiments, where both anchors allow for the flexible member to adjust therealong, a kit may include a first and a second tension-adjusting construct, each anchor inserter having its own tensioning construct 310. In this embodiment, a means of holding both inserters simultaneously may be preferable.

Tension adjusting construct 310 may be configured to engage at least one of the flexible member limbs (20a, 20b) extending from the second anchor 200. Tension adjusting construct may be configured to couple to each flexible member limbs (20a, 20b) separately and independently tension each end one at a time. Tension adjusting construct 310 may be coupled to inserter 300 along the handle 302 or shaft 303. Tension adjusting construct 310 may include at least one handle or actuator 315 for controllably adjusting tension on the flexible member 20. Shown here actuator 315 is a knob 320 that may be rotated. Other mechanisms may include ratcheted sliders, or a pistol grip that is squeezed to move and apply tension on the flexible member 20. Tensioning device 310 may tension continuously, or may include ratchets or a form of step control to tension the flexible member 20 in increments. Increments equivalent to about 1 mm of length of the flexible member 20 may be preferable. Depending on the laxity of the patient joint and surgical technique, it is envisioned that a range of flexible member travel may be between 1 mm-20 mm. Of note, travel or tensioning the flexible member 20 is configured to be bidirectional in that the flexible member 20 may need to increase or decrease tension. Stated in another way, the knob 320 turns both ways.

Figure 3C:
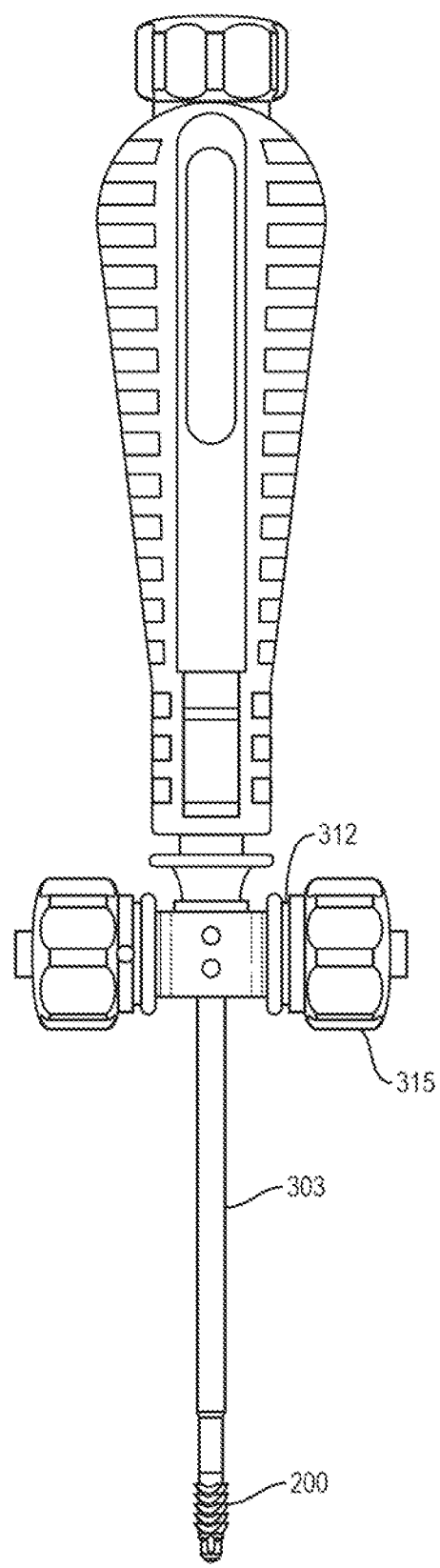
FIG. 3C illustrates another view of the example anchor inserter with a tension adjusting member attached thereto as illustrated in FIG. 3B, in accordance with this disclosure.

Tensioning construct 310 includes a means to engage the flexible member 20. Seen best in FIG. 3C a means of engaging may include a cleat 312 that may be circumferentially disposed around a shaft of the actuator 315. Cleat 312 may define an axial gap along an axis of rotation of the actuator 315 that may be an adjustable gap to selectively grasp and release the flexible member 20. For example, the two opposing sides of cleat 312 may axially move relative to each other to engage and release flexible member limb 20a or 20b. Alternatively, cleat 312 may be formed of a flexible high friction material such as an elastomer, that flexes to receive the flexible member 20 therein and frictionally engages the flexible member limb 20a and/or 20b. In this embodiment, a limb of flexible member 20 may be partially inserted into the cleat 312 and at least partially wrapped circumferential cleat 312. Multiple wraps around the cleat 312 may increase purchase with the flexible member 20.

Tensioning construct 310 may include two independently operated handles 315 that each separately engage one of a first and second limb (20a, 20b) of flexible member 20. In an alternative embodiment, the augmentation construct may include multiple flexible members, a first flexible member and a second flexible member separately formed from each other, each extending and coupled to the plurality of anchors and each handle may separately engage each flexible member. In embodiments where a first end anchor 10 includes a pulley 15, two limbs 20a and 20b of flexible member 20 extend from anchor 10a. During the tensioning operation, there may be unequal tension that develops between the two limbs 20a and 20b. However, due to the pulley 15, the flexible member 20 may slide around pulley 15 and the tension differential may reduce. In other embodiments, a first limb may extend from the first anchor 10 and the second opposing limb may extend from the second anchor, both anchors having a non-locked configuration. In this embodiment, each limb may be tensioned together or individually, to tension from a single end coupled to either a first anchor 10 or the second anchor 200, or both.

Figure 7:
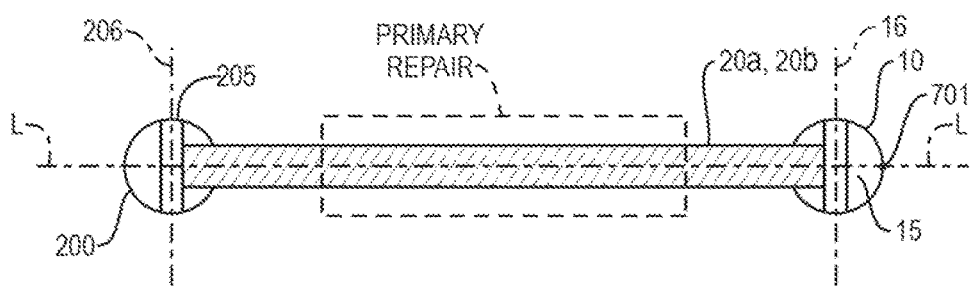
FIG. 7 represents an augmentation construct orientation relative to flexible member and primary repair.

The kit is preferably configured to place and maintain the flexible member 20 along a single plane, with minimum twists or angular departures, thus allowing the flexible member 20 to slide easily and predictably through the respective anchors and distribute the stress to the underlying tissues uniformly. Consider for example when the flexible member is a suture tape, which due to the wider, flatter surfaces may improve stress distribution across the underlying tissue between the two anchors. Twisting of the tape may be palpable by the patent due to the oblong cross section of most tapes. Twisting of the tape may render the uniform the stress distribution less uniform across the underlying tissue. Flexible tape preferably lies flat against the tissue between the two anchors, with minimal to no twisting of the flexible tape. Insertion instruments may therefore include indication means, such as laser marks on the anchor inserter shaft to orient the flexible tape accordingly. FIG. 7 represents a simplified primary repair with an augmentation construct preferably placed over the primary repair. Augmentation construct may define a longitudinal axis L-L that may be approximately parallel with a primary repair where anatomy allows. First end anchor 10 is anchored within the first bone and may be preferably orientated to align the flexible member limbs 20a, 20b with the longitudinal axis L-L, avoiding twists or angular departure of the flexible member path. For example, an inserter for the first anchor (10a or 10b) may include radial indicia on the shaft, to indicate the radial position of anchor pulley 15 and thereby the resultant arrangement of the flexible member 20 when coupled thereto. One possible mark 701 is shown, arranged to align a radial mark with longitudinal axis L-L when in a target location. Mark 701 may be an elongate line along the inserter shaft outer surface, parallel to the shaft longitudinal axis and visible to the user. Stated another way, with reference to FIG. 7, in some embodiments, the pulley 15 may define a pulley axis 16 that may be defined by a transverse through hole axis, or transverse sliding surface; and first end anchor 10 may be preferably rotated during insertion such that pulley axis 16 is perpendicular to axis L-L, indicated by aligning mark 701 with longitudinal axis L-L. Should the first end anchor 10 be inserted by rotation into the first bone, such as anchor 10a, rotation is preferably continued to both insert the anchor 10 and align the pulley axis 16 to be approximately perpendicular to axis L-L. This aligns the flat surfaces of the flexible tape with the underlying tissue. This is also illustrated in FIG. 4D. In the case of a soft anchor 10b, insertion and deployment may not include rotation, and therefore laser marks on the inserter shaft may be aligned before inserting the soft anchor into bone. Although soft anchor may not have a pulley 15, a pulley axis is defined by the loop or bite of flexible member that loops around the pulley portion is still defined. Furthermore, it may be preferable that second end anchor be inserted linearly (without rotation) to reduce any twisting of flexible member 20 during insertion. Second end anchor may include barbs for example, and may be pounded into the second bone. Axis 206 of through-hole 205 may first be aligned to be perpendicular to axis L-L before insertion. Second end anchor may be a soft anchor. Radial marks on the inserter shaft 303 may help orient the second end anchor and flexible member 20 to avoid twists in the flexible member 20.

Figure 4A:
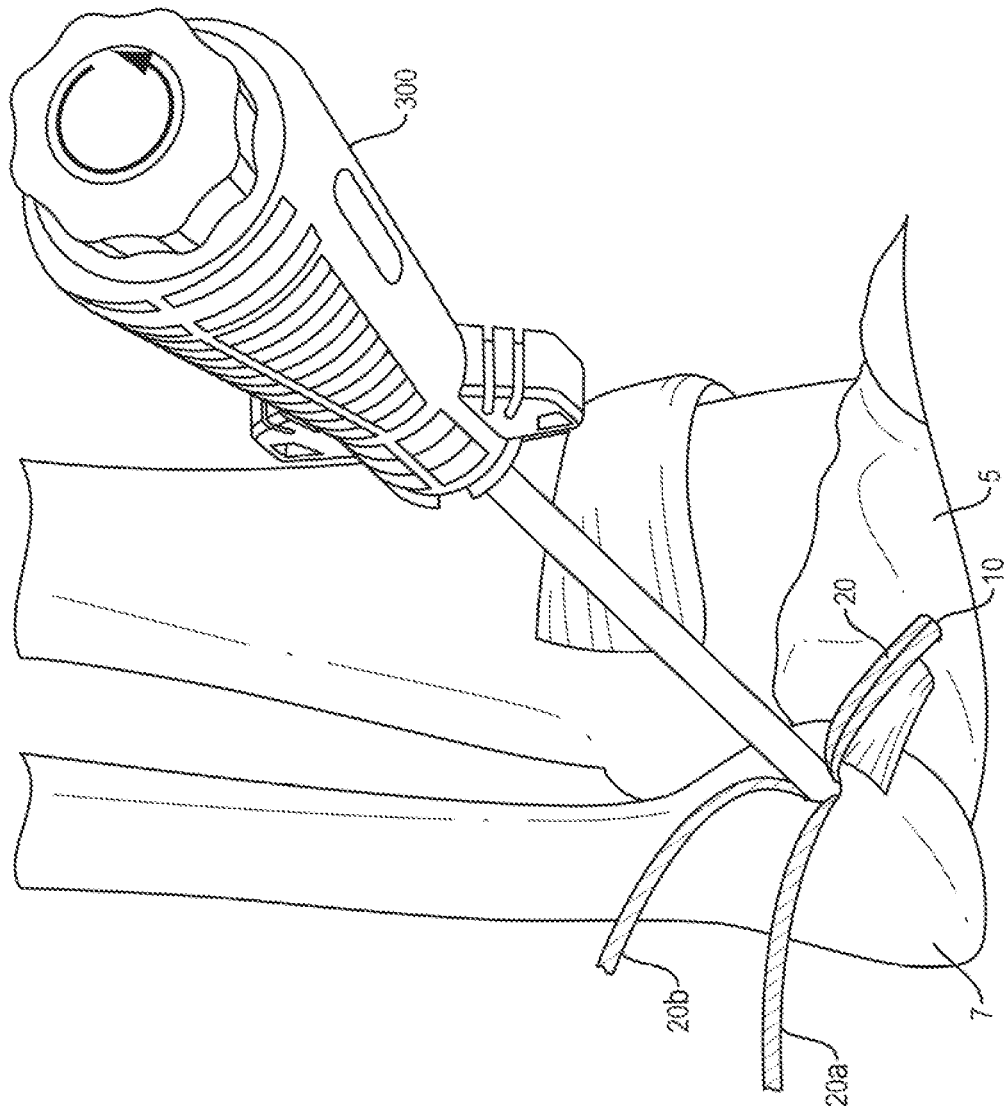
FIGS. 4A-4D illustrate a method of augmenting a primary repair construct, in accordance with this disclosure.
Figure 4C:
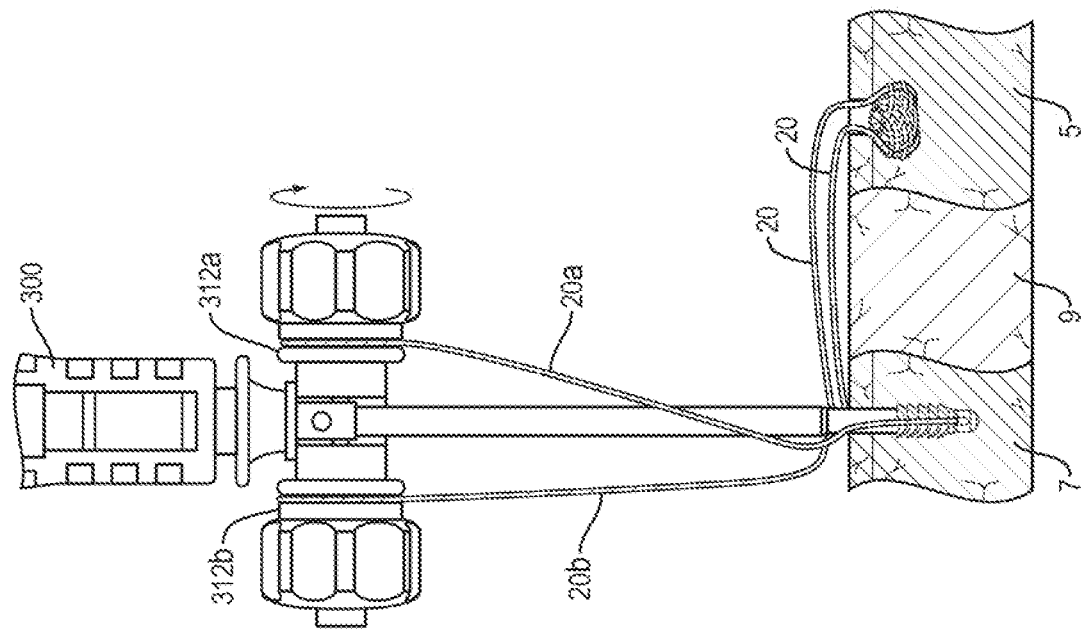
Figure 4B:
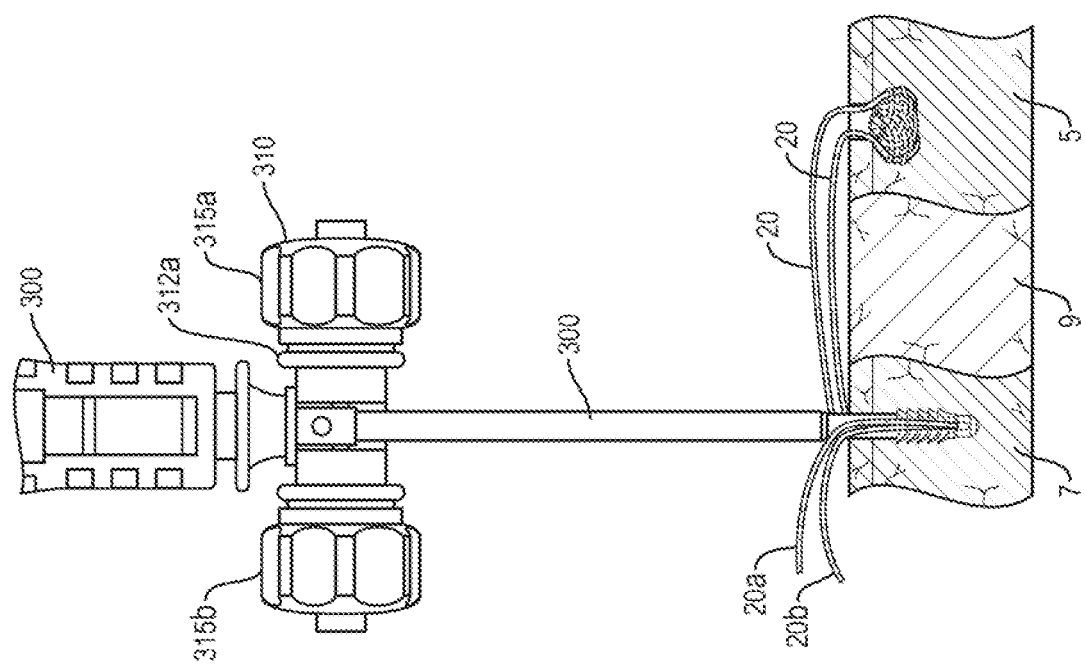
Figure 4D:
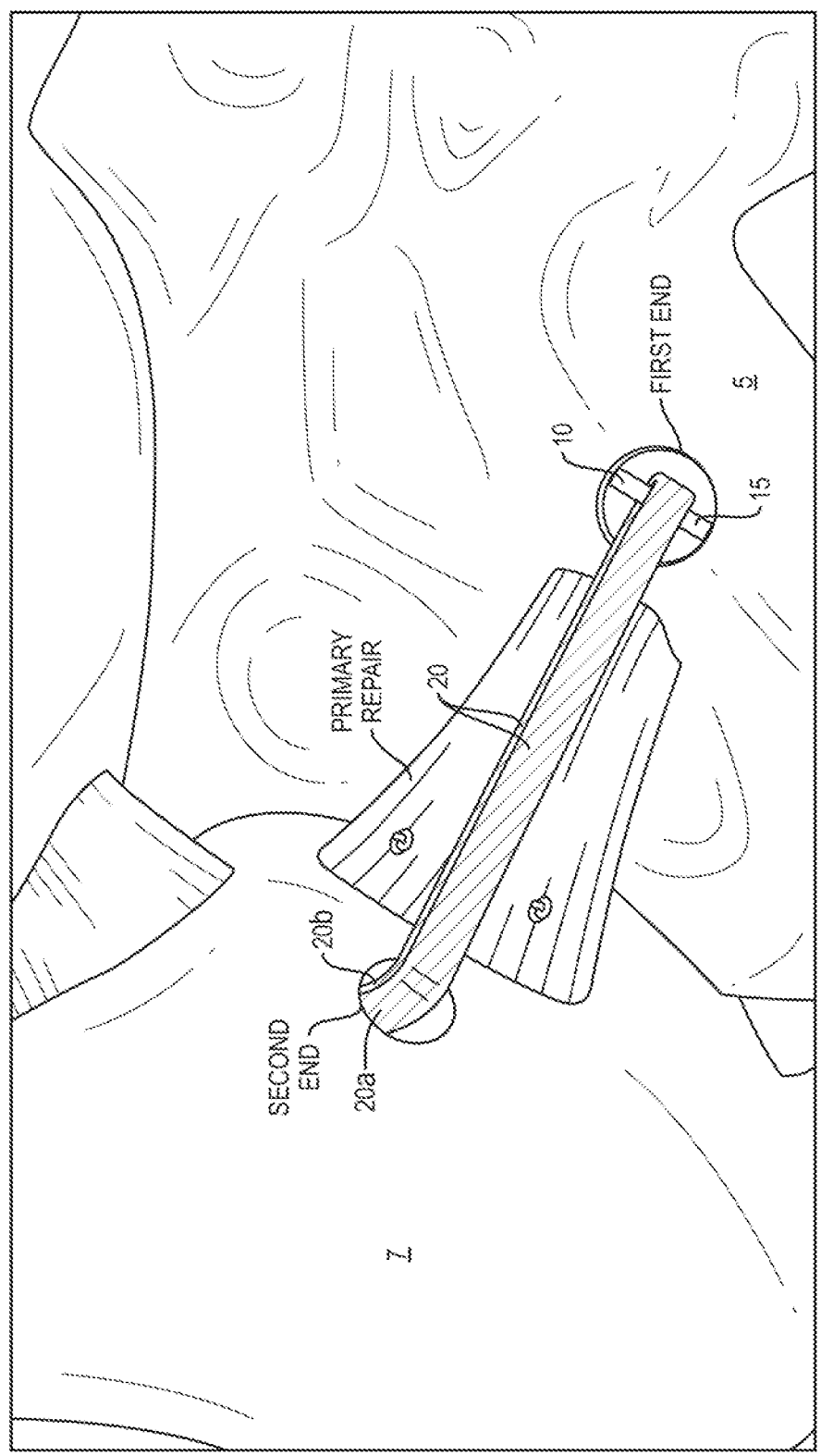

An exemplary method of augmenting a primary tissue repair is illustrated in FIG. 4A-4D. FIG. 4A illustrates a first end anchor 10 already inserted in the talus bone 5 of the foot and ankle joint, near an insertion point of the primary tissue repair (not visible). The primary tissue repair in disposed medially relative to the augmentation and may extend between the talus and fibula. Two flexible member limbs 20a and 20b may then extend across from the talus 5 to the fibula 7 towards an area adjacent a second end of the primary tissue repair. The two limbs 20a, 20b may be suture tape, which preferably lies flat against underlying tissue 9 between the two anchors with minimal twists therealong. Of note, this method may be reversed in that the first end anchor 10 may be placed in the fibula 7 and the second anchor 200 in the talus (if talus is sufficiently thick to avoid intrusion into the subtalar joint). In other example methods for other joint areas, a first end anchor is placed in a first bone while a second end anchor is placed in a second bone, placing the augmentation construct adjacent and along the primary tissue repair and more specifically adjacent opposing ends of the primary tissue repair. Augmentation may align to be approximatively parallel with a longitudinal axis of the primary tissue repair construct. The two limbs 20a and 20b may then be threaded through the second end anchor 200 that may be coupled to an inserter 300. Inserter 300 may then insert the second anchor 200 with the flexible member attached, into a bone tunnel adjacent a second end of the primary tissue repair (FIGS. 4A and 4B). FIG. 4B illustrates a simplified anatomy of the two bones (5 and 7) with a different tissue 9 disposed therebetween. For simplification of the figures, tissue 9 is shown as a single tissue and the primary repair is not shown in FIGS. 4B and 4C.

After insertion of the second anchor, flexible member 20 may have some slack. Flexible member limbs 20a and 20b may be initially tensioned by hand, individually or together to take up some of the slack. Flexible member limbs 20a, 20b may then be coupled to a tensioning adjusting construct 310 (FIG. 4C). Tension adjusting construct 310 may be a separate construct from the anchor inserter 300 and may be coupled to inserter 300 before or after flexible member limbs are coupled thereto. Tension adjusting construct 310 may be coupled to inserter 300 while inserter remains engaged with second anchor 200. Inserter 300 may be provided with construct 310 integrated or pre-attached. If construct 310 is provided separately, construct 310 may include a slot or opening to engage shaft 303 of inserter 300. Slot may be configured to engage shaft 303 while the inserter 300 is coupled to the second anchor 200 and bone. Inserter 300 may include locking features such as holes, slots or protruding key like elements to positively engage with corresponding features on tension adjusting construct 310. It is envisioned that considerable forces on the flexible member 20 may be required and therefore these elements may maintain the tension-adjusting construct in place and prevent the tension-adjusting construct from slipping.

Flexible member limbs 20a and 20b may be coupled to the tension-adjusting construct 310 before assembling the tension-adjusting construct 310 to the inserter 300. Each limb 20a, 20b may be separately coupled to independently actuating portions of the tension adjusting construct 310. For example, limb 20a may be coupled to 312a, and limb 20b may be coupled to 312b. Coupling may include inserting limb 20a into cleat 312a and wrapping limb 20a at least partially around cleat 312a. Handle 315 may then be rotated to reduce the slack on flexible member 20, best shown in FIG. 4C. Tension on flexible member 20 is thereby controllably adjusted.

The target tension on the flexible member depends both on the mechanical properties of the flexible member 20 as well as the degree of inherent laxity of the patient's joint. A flexible member 20 that is a tape may be stiffer for example than a biological construct. Increased number of limbs of the flexible member may be stiffer than a single limb. The method may include tensioning the flexible member limbs 20a, 20b to draw the flexible member 20 through second end anchor 20 and adjust the tension on the flexible member portion disposed between the first and second end anchors to a target tension. The joint may then be articulated to assess the tension between the two anchors over the range of articulation of the joint. The flexible member 20 preferably has a tension that is relatively passive until articulation reaches at least an angular rotation degree of joint articulation that may strain the primary repair construct, such as for example a flexion angle that approximates 40 degrees in the ankle. The surgeon may compare this flexion with the other ankle for example. For some patients a flexion angle of articulation of 30 degrees may be closer to the outer limits inherent for that person. Tension is therefore adjusted on the flexible member 20 via the adjusting construct 301 such that the augmentation construct is relatively passive until articulation closer to the outer limits of articulation particular to that patient, as determined by the surgeon. If the flexible member 20 is too tight, loading may be reduced on the primary repair construct, potentially inhibiting healing and integration of the primary tissue repair construct. Inadequate tension on the flexible member 20 however may permit over-stressing or straining and potential failure of the primary repair construct.

Once this target tension has been achieved, the second end anchor may be locked with a plug member (not shown) advanced through the second anchor 200 and across at least a portion of the through-hole 205, locking the tension on flexible member 20 between the two anchors at this target tension. Advancing the plug may nudge the flexible member 20 slightly further into the bone hole and therefore handle 315 should preferably not be locked in position while locking the second anchor. For example the handle 315 may freely rotate when not being held by user, and may not include a ratcheted wheel or means of locking the handle 315 in place. This allows flexible member 20 to move with the plug as it advances. Once second end anchor 200 has been locked, tension on the flexible member 20 between the two anchors may be checked. If not within acceptable limits, plug may be retracted using the inserter instrument and the tensioning process repeated. Inserter 300 may then be removed, and flexible member limbs trimmed to detach tension-adjusting construct 310 from second end anchor.

FIG. 4D shows the completed augmentation construct relative to an ankle and foot. First end anchor 10 is inserted into a first bone 5, with a pulley 15 and flexible member 20 extending around pulley 15. Pulley 15 may be oriented to align the flexible member 20 to avoid twisting. Second anchor 200 is inserted and recessed within second end of augmentation and flexible member limbs 20a, 20b may be knotlessly locked with second anchor.

In a further example method (not shown) a third anchor may be inserted into a third bone or segment of bone spaced away from the other two anchors and the flexible member coupled thereto, and tension adjusted along the flexible member again. For example the first, second and third anchor may be placed, one each, in one of the talus bone, the fibula bone and the calcaneus bone. One of the anchors may be a non-locking anchor as disclosed herein, which may be adjacent an insertion point of the primary tissue repair. Flexible member 20 may then extend across to the second bone towards an area adjacent a second end of the primary tissue repair. Tension may be adjusted with a tension adjusting construct as disclosed herein, and the flexible member 20 may be locked with the second anchor. Flexible member 20 may also extend across to a third bone (from either the first or the second anchor) and then coupled to a third anchor. Tension may be adjusted as disclosed herein using a tension adjusting construct, and the flexible member 20 may be locked with the third anchor to maintain this tension.

Figure 5A:
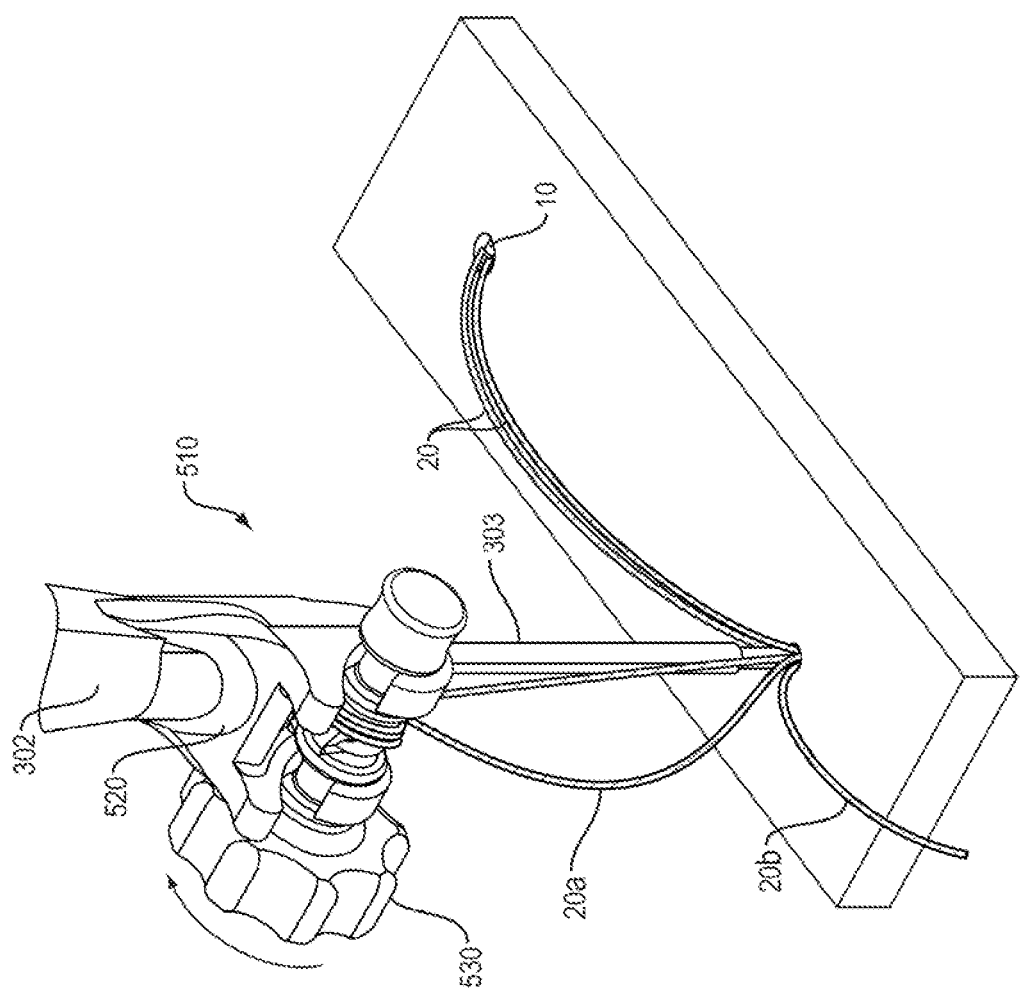
FIGS. 5A and 5B illustrate another insertion instrument with a tension adjustment construct, in accordance with this disclosure.
Figure 5B:
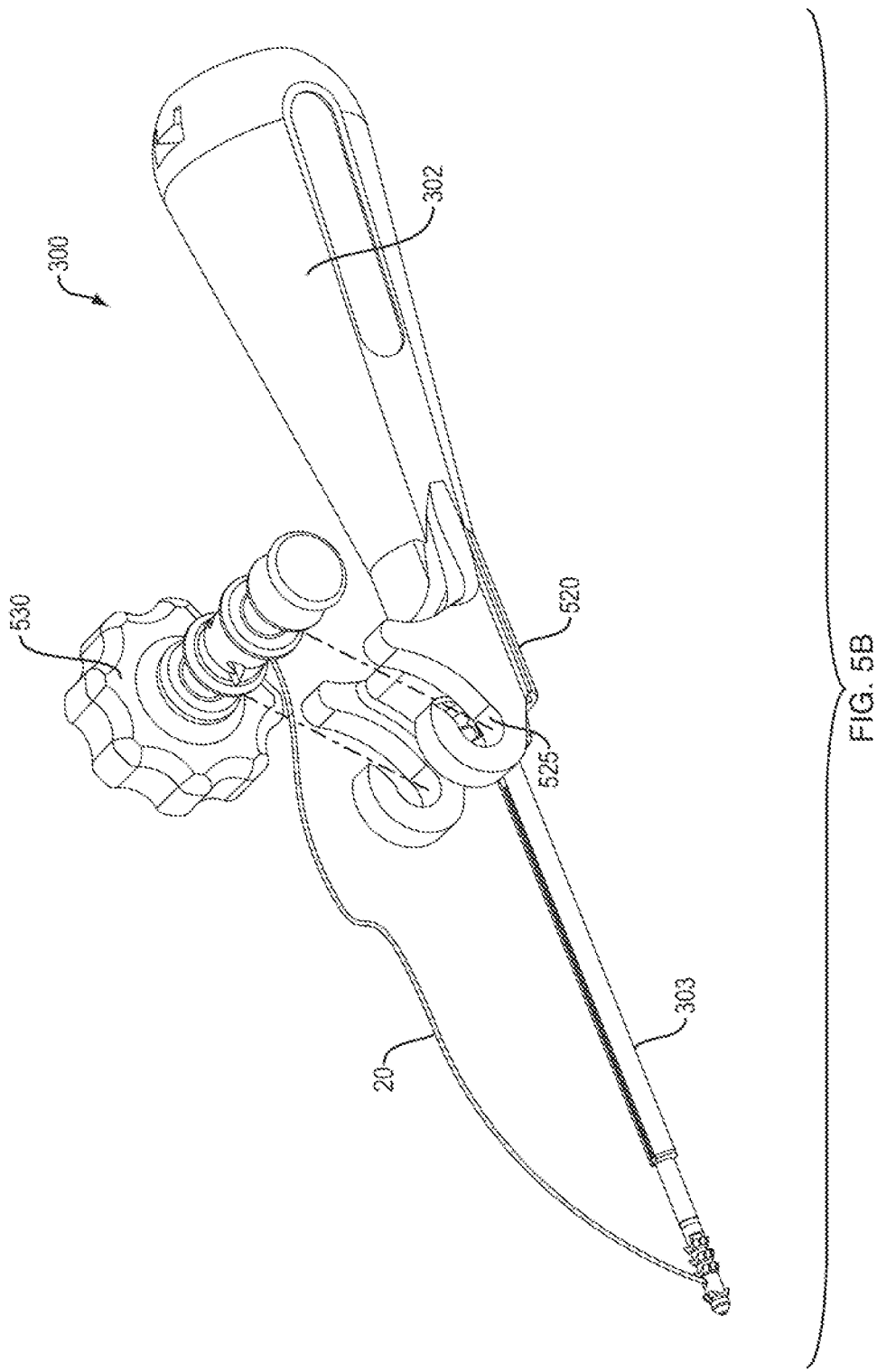

FIGS. 5A and 5B illustrates another example tension-adjusting construct 510 that may be operatively coupled to an anchor inserter 300. Tension adjusting construct 510 may include a base portion 520 and an actuation member 530. In this embodiment, base portion 520 may is integral with handle 302 of inserter 300. In some embodiments, base portion 520 may be assembled to handle 302. Base portion 520 may include a means of engaging actuation member 530, while still allowing actuation member 530 to actuate and thereby apply tension on the flexible member 20. Actuation member 530 may be assembled and disassembled with base portion 520, as desired. Base portion 520 may define at least one slotted opening 525 to receive a shaft 535 of actuation member 530 therein. Slotted opening 525 may define an opening that faces towards the handle 302. Slotted opening 525 may receive a first axial segment(s) of shaft 535. Another axial segment (axially spaced from the first axial segment) of the shaft 535 may operatively couple to the flexible member 20. Other segments of the shaft may limit degrees of freedom of the actuation member 530 while assembled with the base portion 520. For example, shaft 535 may include a plurality of cross section widths, or diameters. At least one of the plurality of cross section widths may be sized to fit within the slotted opening 525, while at least a second of the plurality of cross section widths may be oversized and therefore not fit within the slotted opening 525, and thereby limit axial sliding of the shaft 535 along the longitudinal axis of slotted opening 525. One of the plurality of cross section widths may define a flexible member spool segment 545.

Figure 6A:
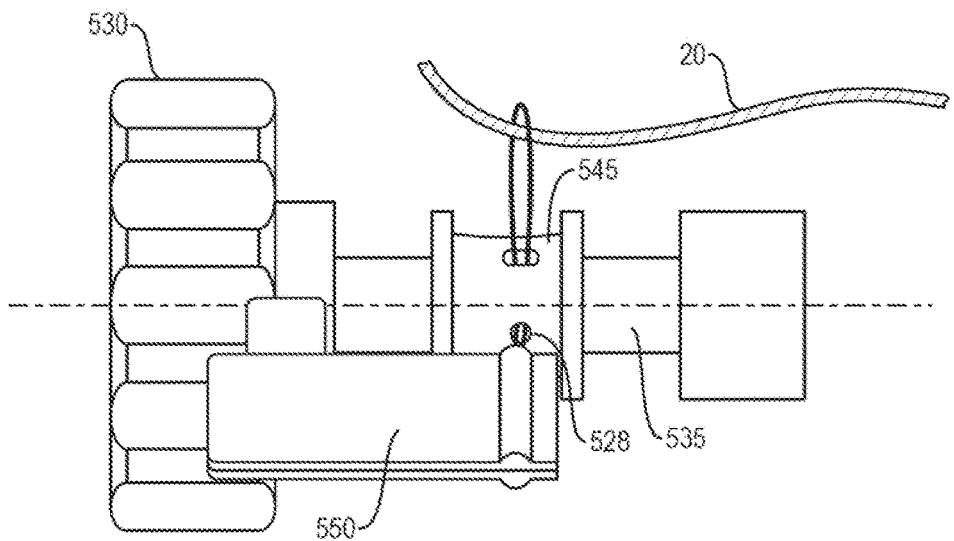
FIGS. 6A and 6B illustrate means of coupling the flexible member to the tension wheel.

Actuation member 530 may include wheel or knob that that may rotated to adjust tension on the flexible member 20. Actuation member 530 may include a means to engage (directly or indirectly) the flexible member 20. Shown in FIG. 6A, the means to engage means may include a tunnel 528 extending through spool segment 545, for receiving a flexible member limb or limbs (20a, 20b) therethrough. Actuation member 530 may be provided with a snare 550 for drawing limb or limbs (20a, 20b) through tunnel 528. Tunnel 528 may extend from an outer circumferential surface of the spool segment 545 to the outer circumferential surface of the spool segment 545 at locations circumferentially spaced from each other. Tunnel 528 may be entirely offset from and thereby not intersect the shaft longitudinal axis. The tunnel 528 may align with a longitudinal axis of inserter shaft 303 and may also align with a longitudinal axis of recess 215. Flexible member limbs 20a, 20b may then extend along recess 215 and along the shaft 303 with minimal twists and changes in orientation. Tunnel 528 preferably maintains the flexible member 20 in a single plane as it extends along the shaft 303, the single plane extending though and parallel to the shaft longitudinal axis. Stated in another way, flexible member 20 preferably does not coil around the inserter shaft 303. Flexible member limbs 20a, 20b may extend along and external to shaft 303, to reduce friction or snagging between flexible member 20 and shaft surfaces, for a smooth uninterrupted tensioning actuation with minimal interference from friction and twisting. The axis of rotation of the actuation member 530 may be perpendicular to longitudinal axis L-L. Actuation member 530 is preferably on the opposite side of inserter 300 to the first anchor 10. Spool segment 545 may maintain the length of flexible member limbs 20a, 20b extending between the second anchor 200 and member 530 substantially within the same vertical plane that extends through both the first and second anchor while inserted into bone. Spool segment 545 may hold the flexible member limbs 20a, 20b substantially along the longitudinal axis of inserter shaft 303, substantially within a plane such that it does not twist around the shaft 303. Keeping the suture limbs 20a, 20b in this orientation helps reduce any frustration with applying tension along the flexible member 20, and keeps all the tension forces along the same plane, as best possible.

Figure 6B:
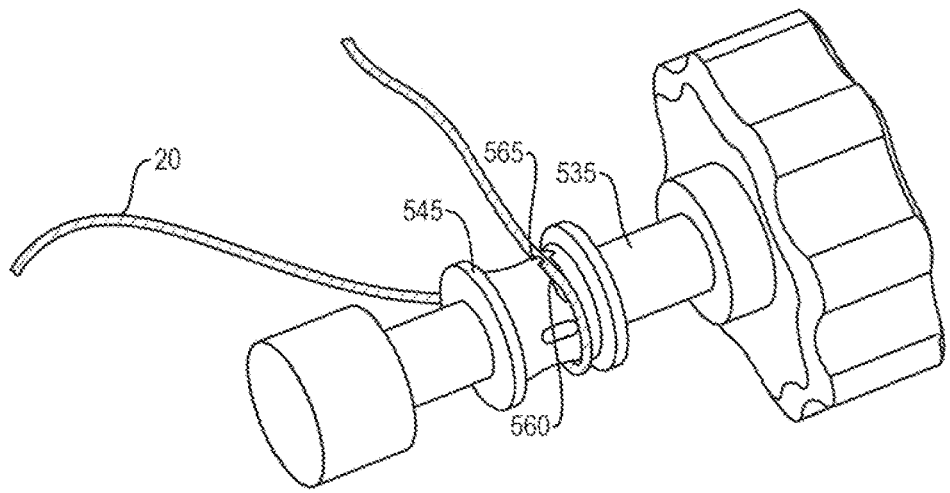

Another example means of engaging the flexible member limbs 20a, 20b with the actuation member 530 is illustrated in FIG. 6B including a circumferential slot 560 with a notch 565. In this embodiment, flexible member 20 may be wrapped around spool segment 545, into and along circumferential slot 560 and slipped under notch 565. Notch 565 may frictionally hold flexible member.

In some embodiments, alternatively to, or in addition to a tensioning adjusting constructs disclosed herein, the flexible member may be tailored for improved primary repair augmentation constructs. For example, the flexible member may be formed to have a modulus of elasticity that more closely resembles native tissues when compared with, for example a suture tape. Flexible member may have an increased degree of elasticity compared with a suture tape which may provide an augmenting construct with a wider range of initial tension and therefore a tensioning construct may have a wider target range for improved outcomes. Flexible member may be absorbable or degradable over a period of time that approximates or slightly lags the healing time of the primary repair. For example, augmentation via the flexible member may diminish over time, the time preferably sufficient for the primary repair construct to significantly heal and integrate with the joint. As a specific example, a primary repair healing time may be approximately 6-8 weeks, and complimentary degradable flexible member may preferably begin to diminish augmentation during the latter part of the 6-8 week period. It is thought that having the primary repair gradually increase its share of the load as it heals, may improve the primary repair outcomes. The inventors envision a flexible member that begins to absorb at some point along the primary repair healing time, and is preferably fully absorbed in less than a year. Stated otherwise, the inventors envision an augmentation construct that degrades over time, to gradually decrease the load absorbed by the augmentation construct and thereby transfer an increased load or strain absorbed by the primary repair construct during the primary repair healing. Two or more flexible members, with differing degradation times may provide a gradual decrease in tension across the augmenting construct over time for example. Alternatively, a single stand of flexible member that preferentially degrades from the outer periphery first may gradually become thinner and inherently increase in elasticity over time, thereby gradually increasing the load on the primary repair construct.

The flexible member may be a collagen-based structure that may have a width, thickness and elasticity that in combination augments the primary repair as disclosed herein. The collagen-based structure may be configured to provide a target set of mechanical properties for improved augmentation of the target joint, and may include customizing a volume of collagen fibrils, forming a collagen composite with other materials or formed in combination with a substrate. Different joints, for example a knee or an ankle may require a different configuration of the collagen based structure in combination with the overall dimensions of the flexible member, to provide the improved augmentation properties for that target joint.

The disclosed kit may augment an adjustable lateral ankle ligament repair. The disclosed kit may be used to augment a Broström procedure. Augmentation may be with a suture tape, such as for example with ULTRABRACE◊ offered for sale by Smith and Nephew. Once the anterior talofibular ligament (ATFL) and calcaneofibular ligament (CFL) are securely repaired (the repair), the disclosed kit may augment the repair and allow the surgeon to tension the construct after the anchors have been inserted to achieve desired tension. The surgeon may customize the tightness of augmentation with the tension adjusting construct.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method of augmenting a primary repair of a ligament of an articulating joint, comprising:
performing the primary repair with a primary repair construct and then augmenting the primary repair construct by;
inserting a first anchor into a first bone adjacent a first anatomical attachment point of the ligament, a flexible member slidingly coupled to the first suture anchor;
slidingly coupling the flexible member to a second anchor, defining an augmenting portion of the flexible member that extends from the first anchor directly to the second anchor, and a flexible member limb extending from the second anchor, the second anchor engaged to a shaft distal end of an anchor inserter;
using the anchor inserter, inserting the second anchor into a second bone adjacent a second anatomical attachment point of the ligament;
operatively coupling the flexible member limb to a tension adjusting actuator of the anchor inserter and with the anchor inserter remaining engaged with the second anchor, moving the actuator to adjust a tension on the augmenting portion of the flexible member, wherein the actuator is configured to both increase and decrease the tension;
articulating the articulating joint while adjusting the tension to a target tension, by increasing and decreasing the tension, the target tension is configured to initiate augmenting once the articulating joint articulates to a degree that places a strain on the primary repair; and
once the target tension has been achieved, knotlessly locking the flexible member with the second anchor.

2. The method of claim 1 wherein the first anchor includes a pulley, and wherein the flexible member is slidingly coupled around the pulley such that two lengths of the flexible member extend from a first anchor proximal end, the augmenting portion comprising the two length of the flexible member, and wherein the slidingly coupling the flexible member to the second anchor includes slidingly coupling the two lengths of the flexible member to the second anchor; and
operatively coupling a second flexible member limb to the tension adjusting actuator of the anchor inserter.

3. The method of claim 1 wherein inserting the second anchor comprises aligning a portion of the flexible member extending directly from the second anchor with an axis extending between the first and second anchor and inserting the second anchor without moving the flexible member out of alignment.

4. The method of claim 1 wherein inserting the first anchor further comprises orienting the first anchor so that the flexible member limb that extends from a proximal end of the first anchor is coincident with an axis that extends through both an insertion location of the first anchor and an insertion location of the second anchor and inserting the first anchor while maintaining the flexible member limb on the axis, avoiding twists or angular departure of the flexible member.

5. The method of claim 1 further comprising engaging the tension-adjusting construct to a second anchor insertion instrument after operatively coupling the flexible member limb thereto.

6. The method of claim 1 wherein the strain at the target tension is configured to improve healing of the primary repair.

7. The method of claim 1 wherein the first anchor is a soft anchor, and wherein the method further comprises deploying the first anchor within the first bone by applying tension on the flexible member limb, the deploying before operatively coupling the flexible member limb to the second anchor.

8. The method of claim 1 wherein the anchor inserter includes a second actuator and wherein the method further comprises;
operatively coupling the flexible member limb directly from the second anchor to the actuator, while the anchor inserter remains operatively coupled to the second anchor; and actuating the second actuator once the target tension has been achieved to knotlessly lock the flexible member.

9. The method of claim 8 further comprising actuating the second actuator to release the knotless unlock on the flexible member and actuating the actuator to readjust the tension on the flexible member and then re-actuating the second actuator to knotless lock the flexible member again.

10. The method of claim 1 further comprising inserting the first and second anchor avoiding rotation.

11. The method of claim 1 further comprising adjusting the tension after the second anchor is inserted.

12. The method of claim 1 wherein the anchor inserter includes a handle, with a shaft extending from a distal end of the handle, the second anchor coupled to a distal end of the shaft, and wherein the actuator is disposed at the handle distal end.

13. The method of claim 1 wherein the actuator includes a shaft rotatably coupled to the anchor inserter, the shaft including an opening to receiving the flexible limb therein, and wherein the method further comprises inserting the flexible limb into the opening after slidingly coupling the flexible member to the second anchor and then rotating the shaft to increase or decrease the tension.

14. A method of augmenting a construct for a primary repair of ligament of an articulating joint, comprising:
inserting a soft anchor coupled to a flexible member into a talus bone and towards a subtalar joint side of the talus bone, at a location adjacent a first anatomical attachment point of the ligament;

deploying the soft anchor within the talus bone, wherein while deploying, a distal end of the soft anchor withdraws from the subtalar joint side of the talus bone;

slidingly coupling the flexible member to a second anchor;

using an anchor inserter, inserting the second anchor into a fibula adjacent a second anatomical attachment point of the ligament associated with the primary repair;

adjusting a tension on the flexible member between the first and second anchor, via rotation of a tensioning wheel operatively coupled to the anchor inserter, wherein adjusting is configured to both increase and decrease the tension on the flexible member between the first and second anchor, and wherein adjusting the tension further comprises;

articulating the articulating joint to apply a first strain on the ligament; and adjusting the tension, by increasing and decreasing the tension, so that the flexible member between the first and second anchor is passive until the ligament is at the first strain; and knotlessly locking the flexible member with the second anchor.

15. The method of claim 14 wherein adjusting the tension is after inserting the second anchor and before knotlessly locking the flexible member with the second anchor.

16. The method of claim 15 further comprising after knotlessly locking the flexible member with the second anchor, knotlessly unlocking the flexible member with the anchor inserter, re-adjusting the tension with the rotation when and the knotlessly relocking the flexible member.

17. The method of claim 14 wherein adjusting the tension on the flexible member comprises sliding the flexible member through the soft anchor.

18. The method of claim 15 further comprising engaging the tension-adjusting construct to a second anchor insertion instrument after operatively coupling the flexible member limb thereto.

19. The method of claim 14 further comprising applying tension to the flexible member to deploy the soft anchor within the talus bone.

20. The method of claim 14 further comprising orienting the flexible member coupled to the second anchor along an axis of augmentation and then inserting the second anchor linearly, so that the flexible member remains on the axis.

21. A method of augmenting a primary repair of a ligament of an articulating joint with a flexible member comprising:

inserting a soft anchor into a first bone from a first side of the first bone and towards an opposing side of the first bone, the inserting adjacent a first anatomical attachment point of the ligament, the flexible member slidingly coupled to the soft anchor;

tensioning the flexible member to deploy the soft anchor, wherein deploying engages a proximal end of the soft anchor against a cortical rim of the first side of the first bone and withdraws the soft anchor away from an internal joint bounded by the opposing side of the first bone, thereby recessing the soft anchor in its entirety from the internal joint;

slidingly coupling the flexible member to a second anchor;

using an anchor inserter, inserting the second anchor coupled to the flexible member into a second bone adjacent a second anatomical attachment point of the ligament, and with the first and second anchor inserted, moving an actuator of the anchor inserter to adjust a tension on a length of the flexible member coupled directly between the first and second anchor; wherein the actuator is coupled to the flexible member such that moving in a first direction increases the tension and moving in a second direction decreases the tension, and wherein adjusting the tension further comprises;

moving the articulating joint to apply a first strain on the ligament, the first strain configured to aid in healing the ligament; and moving the actuator to adjust the tension, including increasing and decreasing the tension, to initiate augmenting at the first strain; and moving a second actuator of the anchor inserter to lock the flexible member with the second anchor, and thereby lock the tension on the length of the flexible member.

* * * * *